United States Patent [19]

Grazioso et al.

[11] Patent Number: 4,607,055
[45] Date of Patent: Aug. 19, 1986

[54] ALIPHATIC ALCOHOL PRODUCTION

[75] Inventors: Michael V. Grazioso, Poughkeepsie, N.Y.; David A. Storm, Montvale, N.J.

[73] Assignee: Texaco Inc., White Plains, N.Y.

[21] Appl. No.: 751,696

[22] Filed: Jul. 3, 1985

[51] Int. Cl.⁴ .............................................. C07C 27/06
[52] U.S. Cl. .................... 518/713; 518/714; 502/206; 502/241; 502/313; 502/314; 502/243
[58] Field of Search ........................ 518/714, 715, 713

[56] References Cited

U.S. PATENT DOCUMENTS 4,492,773  1/1985  Ball et al. ............................ 518/714

FOREIGN PATENT DOCUMENTS 1155463  10/1983  Canada .
  79132   5/1983  European Pat. Off. .
 660678   7/1929  France .

Primary Examiner—Howard T. Mars
Attorney, Agent, or Firm—Robert A. Kulason; James J. O'Loughlin

[57] ABSTRACT

A method is provided for preparing a mixture of lower aliphatic alcohols characterized by containing a substantial proportion of aliphatic alcohols having from 2 to 6 carbon atoms by reacting a mixture of carbon monoxide and hydrogen under suitable conditions of temperature and pressure in the presence of a catalyst comprising molybdenum, a metal from the group consisting of cobalt, iron and nickel, and silver, said catalyst being modified by the addition of a promoter from the class consisting of potassium, cesium and rubidium, said promoter being employed at a concentration ranging from about 1.8 to 13.0 micromoles of said alkali per square meter of surface area of said catalyst.

21 Claims, No Drawings

ALIPHATIC ALCOHOL PRODUCTION

BACKGROUND OF THE INVENTION

1. Field of the Invention

This invention relates to a process for preparing lower aliphatic alcohols. More particularly, this invention relates to the production of a mixture of lower aliphatic alcohols characterized by containing a substantial proportion of alcohols having from 2 to 6 carbon atoms.

Lower aliphatic alcohols have been proposed as fuel extenders or as replacements for gasoline for fueling internal combustion engines. Certain mixtures of lower aliphatic alcohols have the EPA approval for use and are currently being marketed in the United States. The lower aliphatic alcohols can be produced from domestically available non-petroleum sources, and their use in fuels would serve to lessen the dependence of the nation on imported petroleum and petroleum products.

Hydrogen and carbon monoxide, or a synthesis gas mixture of hydrogen and carbon monoxide, can be reacted to form lower aliphatic alcohols. A synthesis gas feed stream can be produced from non-petroleum sources, such as coal, biomass or other hydrocarbonaceous materials. The synthesis gas mixture itself is produced in a partial oxidation reaction of the hydrocarbonaceous material in commercially available processes such as coal gasification.

Numerous catalytic processes have been studied in attempts to provide a viable process for the production of aliphatic alcohols from synthesis gas or from a mixture of hydrogen and carbon monoxide. Heretofore, the emphasis has been primarily directed to the production of methanol. In contrast, the present process is directed to a method for producing an alcohol mixture containing a substantial amount of aliphatic alcohols having from 2 to 6 carbon atoms. Under selected reaction conditions, this process is effective for producing a fraction of higher aliphatic alcohols, i.e. an alcohol fraction consisting of $C_2$ to $C_6$ alcohols, which represents the major or predominant alcohol production in this process.

2. Disclosure Statement

U.S. Pat. No. 1,201,850 discloses a method for the production of hydrocarbons and oxygenated compounds of hydrocarbons by passing an oxide of carbon and hydrogen over a heated catalytic agent under a pressure exceeding 5 atmospheres. A number of catalytic materials are disclosed as well as the fact that a basic compound, such an an alkaline metal hydroxide, can be used with the prescribed catalytic agents.

U.S. Pat. No. 1,625,929 discloses a process for producing methanol in which the catalyst contains copper, cobalt and a metallic halide.

U.S. Pat. No. 3,345,427 discloses a dehydrogenation catalyst and process in which the catalyst consists of nickel, molybdenum and alkali metal oxides on an alumina support.

U.S. Pat. No. 4,096,164 discloses a process for reacting hydrogen and carbon monoxide in the presence of a solid catalyst comprising rhodium with molybdenum or tungsten to produce two carbon atom oxygenated hydrocarbons in which ethanol is the major component.

U.S. Pat. No. 4,199,522 discloses a Fischer-Tropsch process for producing olefins and this disclosure is incorporated herein by reference.

U.S. Pat. Nos. 4,235,801 and 4,246,186 disclose the production of alcohols from a mixture of carbon monoxide and hydrogen in the presence of a rhenium catalyst.

U.S. Pat. No. 4,380,589 discloses a Fischer-Tropsch process for producing hydrocarbons with improved selectivity to $C_2$-$C_4$ olefins by contacting hydrogen and carbon monoxide in the presence of a catalyst. The catalyst disclosed comprises molybdenum, a promoter comprising alkali or alkaline earth metal, and a binder comprising an iron-containing calcium aluminate cement.

EPA 119609 discloses a process for producing alcohols from synthesis gas using a catalyst containing molybdenum with tungsten, rhenium and an alkali metal. This disclosure is incorporated herein by reference. E.P. 79132 discloses a similar process in which the catalyst contains rhenium, molybdenum and potassium.

Co-assigned application Ser. No. 728,636 filed on Apr. 29, 1985 is directed to a process for producing lower aliphatic alcohols from a mixture of carbon monoxide and hydrogen in the presence of a catalyst comprising molybdenum and a metal selected from the group consisting of cobalt, iron and nickel which has been promoted by an alkali metal selected from the group consisting of potassium, cesium and rubidium and this disclosure is incorporated herein by reference.

Previous catalytic processes have been notably effective for converting carbon monoxide and hydrogen feedstocks into hydrocarbons or methanol, but none have been particularly effective for providing a substantial yield of a lower aliphatic alcohol mixture at a moderate reaction temperature characterized by producing a significant amount of alcohols having from 2 to 6 carbon atoms as compared by the coproduced methanol.

SUMMARY OF THE INVENTION

It has been discovered that a mixture of carbon monoxide and hydrogen can be reacted to form a mixture of lower aliphatic alcohols containing a substantial amount of aliphatic alcohols having from 2 to 6 carbon atoms. This reaction is conducted by contacting a feed mixture, such as synthesis gas, with a novel catalyst composition which exhibits good selectivity for the production of $C_2$-$C_6$ aliphatic alcohols. The novel catalyst composition comprises a mixture of molybdenum, a metal from the group consisting of cobalt, iron and nickel, and silver which has been modified or promoted with an alkali metal from the class consisting of potassium, cesium and rubidium. The use of silver in this promoted catalyst composition to make the indicated alcohols is unique. Surprisingly, the silver-containing promoted catalyst gives a process with a high selectivity for the desired alcohols at a relatively low reaction temperature when employed within critical limits of from about 0.5 to 5 weight percent of silver, as silver, in the catalyst composition.

DETAILED EMBODIMENTS OF THE INVENTION

In accordance with this invention, a mixture of carbon monoxide and hydrogen as, for example, a synthesis gas mixture of said reactants, is reacted over a catalyst comprising molybdenum, a metal from the group consisting of cobalt, iron and nickel, and silver, which has been modified by the addition of a promoter from the group consisting of potassium, cesium and rubidium, said promoter being employed at a concentration ranging from about 1.8 to 13.0 micromoles of alkali per square meter of surface area of the catalyst. The silver component and the concentrations of silver and of the promoter on the catalyst are critical in this process.

The catalyst can be prepared in a number of ways known in the art. In general, the use of a catalyst support or carrier comprising a relatively refractory, porous, adsorptive and high surface area material is preferred. Conventional carriers or supports, such as alumina, silica, titania, magnesia, silica-alumina and boron phosphates, are suitable support materials for preparing the catalyst for this process. The disclosure in U.S. Pat. No. 4,098,683 is illustrative and is incorporated herein by reference.

A preferred method for preparing the catalyst is to impregnate a carrier, such as alumina, with a source of molybdenum generally in the form of a soluble salt, then with a metal from the class of cobalt, nickel and iron, generally also in the form of a soluble salt and finally with silver in the form of a soluble salt. The impregnation of the carrier with the catalyst metals can be done simultaneously or sequentially. The impregnated carrier is dried and then calcined according to known procedures.

The basic catalyst composition comprises from about 5 to 50 weight percent of molybdenum calculated as molybdenum trioxide, from about 0.3 to 15 weight percent of a metal from the group consisting of cobalt, nickel and iron calculated as the respective oxide CoO, NiO or $Fe_2O_3$ or a mixture thereof, and from about 0.5 to 5 weight percent of silver as silver metal, with the balance being the support. A preferred catalyst composition comprises from about 7 to 30 weight percent of molybdenum trioxide, from about 0.5 to 10 weight percent of cobalt, nickel, or iron oxide or a combination thereof and from about 0.5 to 5 weight percent of silver. Still more preferred is a catalyst comprising from about 7 to 12 weight percent molybdenum, from about 1.5 to 5 weight percent of a metal from the group consisting of cobalt, iron and nickel or a mixture thereof and from about 1 to 4 weight percent of silver, all calculated as hereinabove described. Alternatively, a commercially available catalyst comprising molybdenum, one or more of the metals from the class consisting of cobalt, nickel and iron, and silver meeting the foregoing specifications can be employed.

The catalyst should have a surface area of 125 $m^2/gm$ (square meters per gram of catalyst) or more. A more effective catalyst will have a surface area from about 150 to 350 $m^2/gm$ and the most preferred will have a surface area from about 160 to 300 $m^2/gm$.

It is essential that the catalyst be modified, i.e. treated on impregnated, with an alkali metal promoter from the group of potassium, cesium or rubidium generally in the form of a salt. The critical concentration range for the alkali promoter is an amount from about 1.8 to 13.0 micromoles of alkali per square meter of surface area of the catalyst. A preferred alkali promoter concentration is from 2.2 to 10.0 micromoles of alkali per square meter of catalyst surface area with the most preferred alkali promoter concentration being from about 2.5 to about 9.0 micromoles of alkali per square meter of catalyst surface area. The treated or modified catalyst is then subjected to reduction with hydrogen gas generally by heating the promoted catalyst at a temperature between about 300° and 500° C. for an extended period, usually 2 to 8 hours.

The carbon monoxide and hydrogen employed to form the lower aliphatic alcohols in this process can be provided from any available source. One particularly useful source is synthesis gas produced in the gasification of hydrocarbonaceous materials, such as coals and biomass. An effective gasification process is described in U.S. Pat. No. 3,544,291 wherein a hydrocarbonaceous fuel is partially oxidized with a free oxygen-containing gas in a gas generator. In general, the mole ratio of hydrogen to carbon monoxide employed in this process should range from about 0.1 to 50 moles of hydrogen per mole of carbon monoxide with the preferred ratio being from about 0.5 to 20 moles of hydrogen per mole of carbon monoxide.

The reaction conditions for effecting the conversion of the carbon monoxide-hydrogen feed into lower aliphatic alcohols employing the prescribed catalyst of the invention include a reaction temperature ranging from about 240° to about 400° C. with a preferred temperature range being from about 290° to about 350° C., with the most preferred temperature being from about 300° to 330° C. The effective pressure range for this process is from about $3.4 \times 10^6$ Pa (500 psi) to about $2.4 \times 10^7$ Pa (3500 psi). The preferred pressure range is from about $5.1 \times 10^6$ Pa (750 psi) to about $1.7 \times 10^7$ Pa (2500 psi).

The space velocity employed to effect the conversion of carbon monoxide and hydrogen over the prescribed catalyst to the aliphatic alcohols is a vital feature of this process. In general, the space velocity, that is the volume of gas passed through a given volume of catalyst per hour expressed as GHSV($hr^{-1}$), must be at least 1000. A preferred range is from about 5000 to about 50,000. A highly effective process is realized when the space velocity employed ranges from about 10,000 to about 30,000. Under preferred conditions the ratio of weight percent of $C_2$-$C_6$ alcohols to weight percent methanol can exceed 1, and more preferably can be from 1.25 to 2.

The present invention is more fully described in the following Examples. The reactor used for this work was a 1" I.D. type 316 stainless steel tube. 10 cc of the catalyst was diluted with 90 cc of alpha alumina and packed into the reactor. The catalyst was reduced for 4 hours, at 400° C., at a pressure of 1500 psig with a flow of hydrogen gas at 2.5 liters per minute. The catalyst was then cooled to reaction temperature and subjected to a mixture of hydrogen and carbon monoxide in a ratio of 2:1, at a pressure of 1500 psig and a GHSV of 28,000 $hr^{-1}$.

The product emerging from the reactor was sent through a condensor which liquefied the alcohols and water products. The resulting liquid was analyzed by gas chromatography. The non-condensable gas was also analyzed by gas chromatography.

The selectivity to hydrocarbons, methanol, and alcohols containing 2 to 6 carbon atoms is set forth in the table. The alcohol production in grams of alcohol per gram of catalyst per hour is also set forth in the table. Selectivity is defined as the percentage of carbon atoms converted from carbon monoxide to a specified compound or compounds other than $CO_2$.

EXAMPLE 1

(cat.37432-48-7, run #G85-2)

A catalyst was prepared by impregnating a commercially available catalyst comprising cobalt and molybdenum on an alumina carrier first with a solution of silver nitrate, and after calcination with a solution of potassium carbonate. The commercial catalyst was made by Armak catalyst division, Pasadena, Tex. and sold under the name Ketjen KF124LD. The silver nitrate solution was made by dissolving 0.39 grams of silver nitrate in 28 cc of distilled water which was then added to 50.0 grams of the KF 124LD catalyst. The impregnated catalyst was then dried and calcined at 450° C. for several hours. After calcination a solution of 8.0 grams of potassium carbonate, dissolved in 30 cc of distilled water was added to the above catalyst. This catalyst was then dried at 125° C. for several hours. The approximate chemical analysis of the catalyst is set forth in the table under Example 1.

EXAMPLE 2

(cat.37432-48-16, run #G85-3)

Another catalyst was made as in Example 1, however, the catalyst was impregnated with a solution made by dissolving 0.79 grams of silver nitrate in 28 cc of distilled water, which was added to 50.0 grams of the KF 124LD catalyst. After drying and calcination a solution of 8.0 grams of potassium carbonate, dissolved in 30 cc of distilled water, was added to the above catalyst. The catalyst was then dried at 125° C. for several hours. The approximate chemical analysis is set forth in the table under Example 2.

EXAMPLE 3

(cat.37432-48-19, run #G85-4)

Another catalyst was made as in Example 1, however, the catalyst was impregnated with a solution made by dissolving 1.57 grams of silver nitrate in 28 cc of distilled water, which was added to 50.0 grams of the KF 124LD catalyst. After drying and calcination a solution of 8.0 grams of potassium carbonate, dissolved in 30 cc of distilled water, was added to the above catalyst. The catalyst was then dried at 125° C. for several hours. The approximate chemical analysis is set forth in the table under Example 3.

EXAMPLE 4

(cat.37673-7-23, run #G85-21)

Another catalyst was made as in Example 1, however, the catalyst was impregnated with a solution made by dissolving 3.1 grams of silver nitrate in 28 cc of distilled water, which was added to 50.0 grams of the KF 124LD catalyst. After drying and calcination a solution of 8.0 grams of potassium carbonate, dissolved in 30 cc of distilled water, was added to the above catalyst. The catalyst was then dried for several hours. The approximate chemical analysis is set forth in the table under Example 4.

EXAMPLE 5

(cat.37673-7-31, run #25)

Another catalyst was made as in Example 1, however, the catalyst was impregnated with a solution made by dissolving 4.7 grams of silver nitrate in 28 cc of distilled water, which was added to 50.0 grams of the KF 124LD catalyst. After drying and calcination a solution of 8.0 grams of potassium carbonate, dissolved in 30 cc of distilled water, was added to the above catalyst. The catalyst was then dried for several hours. The approximate chemical analysis is set forth in the table under Example 5.

EXAMPLE 6

(comparative, cat.37432-2, run #G84-66)

A catalyst was made as in Example 1, however, no silver nitrate was added. 30 grams of potassium carbonate, dissolved in 90 cc of distilled water, was added to 170 grams of the KF 124LD catalyst. This was then dried at 135° C. for several hours. The chemical analysis of this catalyst is set forth in the table under Example 6.

TABLE I

| | EXAMPLE | | | | | |
|---|---|---|---|---|---|---|
| | 1 | 2 | 3 | 4 | 5 | 6 (Comp.) |
| Catalyst Comp. | | | | | | |
| Wt % $MoO_3$ | 10.0 | 9.8 | 9.7 | 10.4 | 10.2 | 10.6 |
| CoO | 3.4 | 3.4 | 3.4 | 3.4 | 3.3 | 3.4 |
| Ag | 0.48 | 0.94 | 1.9 | 3.5 | 5.1 | — |
| $K_2O$ | 10.5 | 10.0 | 10.3 | 9.5 | 9.3 | 10.7 |
| $H_2/CO$ Ratio | 2.0 | 2.0 | 2.0 | 2.0 | 2.0 | 2.0 |
| Temp. °C. | 315 | 315 | 315 | 315 | 315 | 315 |
| GHSV($HR^{-1}$) | 28,000 | 28,000 | 28,000 | 28,000 | 28,000 | 28,000 |
| Pressure Pa | $1 \times 10^7$ | $1 \times 10^7$ | $1 \times 10^7$ | $1 \times 10^7$ | $1 \times 10^7$ | $1 \times 10^7$ |
| $\frac{\mu\text{-Mole K}}{M^2}=$ | 8.1 | 7.7 | 7.9 | 7.3 | 7.2 | 8.2 |
| Selectivity (%) To: | | | | | | |
| $CO_2$ | 48 | 48 | 48 | 45 | 49 | 59 |
| $C_1$–$C_6$ H.carbons | 27 | 25 | 24 | 28 | 28 | 25 |
| MeOH | 8 | 8 | 8 | 9 | 8 | 4 |
| $C_2$–$C_6$ Alcohols | 17 | 19 | 21 | 17 | 16 | 11 |
| Alcohol Prod. (G/G-hr) | 0.19 | 0.26 | 0.29 | 0.28 | 0.21 | 0.07 |
| $\frac{C_2\text{-}C_6 \text{ Alc. Wt \%}}{\text{MeOH Liq. Wt \%}}=$ | 2.1 | 2.4 | 2.6 | 1.9 | 2.0 | 2.7 |
| $C_2$ + Alc. Prod. (G/G-hr) | 0.13 | 0.18 | 0.21 | 0.18 | 0.14 | 0.05 |

The foregoing examples demonstrate that a process for the production of lower aliphatic alcohols from a mixture of carbon monoxide and hydrogen within the critical parameters for the prescribed promoted catalyst has high selectivity for producing a mixture of $C_2$-$C_6$ aliphatic alcohols.

What is claimed is:

1. A method for preparing lower aliphatic alcohols characterized by producing a substantial proportion of aliphatic alcohols having from 2 to 6 carbon atoms which comprises reacting carbon monoxide and hydrogen in the presence of a catalyst at a temperature from about 240° to about 400° C., a pressure from about 500 to about 3000 psi and a gas hourly space velocity of at least 1000, said catalyst consisting essentially of from about 5 to about 50 weight percent of molybdenum calculated as $MoO_3$, from about 0.3 to about 15 weight percent of a metal selected from the group consisting of cobalt, iron and nickel, calculated as CoO, $Fe_2O_3$ or NiO, respectively, and from about 0.5 to 5 weight percent of silver, calculated as Ag, and the balance a support, said catalyst being modified by the addition of an alkali metal promoter from the class consisting of potassium, cesium and rubidium in an amount ranging from about 1.8 to 13.0 micromoles of said alkali metal per square meter of catalyst surface area.

2. A method according to claim 1 in which said catalyst contains from about 1 to 4 weight percent of said silver.

3. A method according to claim 1 in which said catalyst contains from about 2.5 to 5 weight percent of said silver determined as Ag.

4. A method according to claim 1 in which said reaction is conducted at a temperature ranging from about 290° to 350° C.

5. A method according to claim 1 in which said reaction is conducted at a temperature ranging from about 300° to 330° C.

6. A method according to claim 1 in which said alkali metal promoter is employed at a concentration ranging from about 2.2 to 10.0 micromoles per square meter of catalyst surface area.

7. A method according to claim 6 in which said promoter is employed at a concentration ranging from about 2.5 to 9.0 micromoles.

8. A method according to claim 1 in which said promoter is potassium.

9. A method according to claim 1 in which said promoter is cesium.

10. A method according to claim 1 in which said support is selected from the class consisting of alumina, silica, titania, magnesia, silica-alumina and boron phosphates.

11. A method according to claim 1 in which said support is alumina and comprises from about 60 to 80 weight percent of said catalyst.

12. A method according to claim 1 in which said gas hourly space velocity ranges from about 5,000 to 50,000.

13. A method according to claim 1 in which the gas hourly space velocity ranges from about 10,000 to about 30,000.

14. A method according to claim 1 in which the molar ratio of hydrogen to carbon monoxide ranges from about 20:1 to 0.5:1.

15. A method according to claim 1 in which said catalyst has a surface area greater than about 125 $m^2$/gm.

16. A method according to claim 1 in which said catalyst has a surface area ranging from about 150 to 350 $m^2$/gm.

17. A method according to claim 1 in which the weight ratio of the aliphatic alcohols having from 2 to 6 carbon atoms to methanol is at least 1.

18. A method according to claim 1 in which the weight ratio of the $C_2$-$C_6$ alcohols to methanol is in the range of 1.25-2:1.

19. A method according to claim 1 in which the metal components of a catalyst are in the free or combined form.

20. A method for preparing lower aliphatic alcohols in which the weight ratio of the $C_2$-$C_6$ alcohols to methanol is greater than 1 which comprises reacting carbon monoxide and hydrogen in the presence of a catalyst at a temperature from about 300° to 330° C., a pressure from about 750 to 2500 psi and a gas hourly space velocity in the range from about 10,000 to 30,000, said catalyst consisting essentially of from about 7 to 30 weight percent of molybdenum calculated $MoO_3$, from about 0.5 to 10 weight percent of a metal or mixture of metals selected from the group consisting of cobalt, iron and nickel calculated as CoO, $Fe_2O_3$ or NiO respectively, and from about 1 to 4 weight percent of silver as Ag, and the balance an alumina support, said catalyst being modified by the addition of an alkali metal promoter from the class consisting of potassium, cesium and rubidium in an amount ranging from about 2.2 to 10.0 micromoles of said alkali metal per square meter of catslyst surface area.

21. A method according to claim 20 in which said alumina support comprises from about 60 to 80 weight percent of said catalyst.

* * * * *